US007407794B2

(12) United States Patent
Elmer et al.

(10) Patent No.: US 7,407,794 B2
(45) Date of Patent: Aug. 5, 2008

(54) BIOLOGICAL CONTROL OF PLANT DISEASES

(75) Inventors: Philip George Elmer, Hamilton (NZ); Tony Reglinski, Hamilton (NZ); Robert Anthony Hill, Taupiri (NZ)

(73) Assignee: The Horticulture and Food Research Institute of New Zealand Limited, Auckland (NZ)

( * ) Notice: Subject to any disclaimer, the term of this patent is extended or adjusted under 35 U.S.C. 154(b) by 538 days.

(21) Appl. No.: 10/480,811

(22) PCT Filed: Jun. 15, 2001

(86) PCT No.: PCT/NZ01/00111

§ 371 (c)(1), (2), (4) Date: Dec. 15, 2003

(87) PCT Pub. No.: WO02/102161

PCT Pub. Date: Dec. 27, 2002

(65) Prior Publication Data

US 2005/0063955 A1 Mar. 24, 2005

(51) Int. Cl.
*C12N 1/14* (2006.01)
*A01N 63/04* (2006.01)

(52) U.S. Cl. .................. 435/254.1; 424/93.5; 424/93.3; 435/252.4; 504/117

(58) Field of Classification Search ....................... None
See application file for complete search history.

(56) References Cited

OTHER PUBLICATIONS

Kohl et al.Plant Dis. 84:569-573.*
Chong et al. (New Zealand Journal of Botany, 1982, vol. 20 : 187-189).*
http://www.atcc.org, accessed Aug. 18, 2006.*
Levinskaite et al, Biologija, No. 3-4, 1995, pp. 150-153, Effect of chromium on soil fungi.
Peciulyte et al, Biologija, No. 3-4, 1995, pp. 154-158, Studies on accumulation of chromium by fungal biomass.
Fisher et al, Trans of the British Mycological Soc, 89(2), pp. 246-249, 1987, Location of fungal endophytes in tissues . . . .
Papavassiliou et al, Mycopathologia, 57(1), pp. 31-34, 1975, The atmospheric fungal flora of the Athens metropolitan area.
Walter et al, Proc of the NZ Plant Protection Conf, 49th Issue, p. 316, Saprophytic suppression of *Botrytis cinerea* . . . .
Hill et al, Biol Act Nat Prod: Agrochem (Symp 214th), 1999, pp. 201-210, Practical natural solutions for plant disease control.
Boyd-Wilson et al, Proc 51st NZ Plant Protection Conf., 1998, pp. 96-101, Persistence and survival of saprophytic fungi . . . .
Elad et al, Euro Jour of Plant Pathology, 100(5), 1994, pp. 315-336, Control of infection and sporulation of *Botrytis* . . . .
Kohl et al, Phytopathology, 88(6), 1998, pp. 568-575, Biological control of *Botrytis cinerea* in cyclamen with . . . .
Elmer et al, Euro Jour of Plant Pathology, 104(5), 1998, pp. 435-447, The survival and saprophytic competitive ability of . . . .
Boff, Epidemiology and Biological Control of Grey Mould in Annual Strawberry Crops, 2000, 128 pgs., The Netherlands.
Butler et al, Pl. Path. 28, 1979, pp. 96-97, Leaf spot on cumcumber caused by *Ulocladium actrum*.
Domsch et al, Copendium of Soil Fungi, vol. 1, p. 825, 1980, *Ulocladium* Preuss 1851.
Eden et al, Plant Pathology 45, 1996, pp. 276-284, Biological control of *Botrytis* stem infection of greenhouse tomatoes.
Elmer et al, European Journal of Plant Pathology, 1995, Abstract page, Progress Towards Biological Control of *Botrytis cinerea* . . . .
Hill et al, NZ Wine Grower Ann Res Suppl 1996/97, Proj No. 13, New Methods for Controlling Botrytis in Grapes.
Köhl et al, Phytopathology, vol. 85, No. 4, 1995, pp. 393-401, Effect of *Ulocladium atrum* and Other Antagonists on . . . .
Köhl et al, European Journal of Plant Pathology 101, pp. 627-637, 1995, Effect of interrupted leaf wetness periods on . . . .
Köhl et al, Phytopathology, vol. 88, No. 6, pp. 568-575, 1998, Biological Control of *Botrytis cinerea* in Cyclamen with . . . .
Lennartz et al, Med Fac Landouww Univ Gent, 63/3b, 1998, pp. 963-970, Biocontrol of *Botrytis Cinerea* on Grapevine and . . . .
Michailides et al, Plant Disease, vol. 84, No. 3, pp. 208-221, 2000, Botrytis Gray Mold of Kiwifruit Caused by *Botrytis* . . . .
Mimbela-Leyva et al, Trop. Sci. 17(2), 1975, pp. 61-74, Quality problems of South America honeydew melons imported into Britain.
Nair et al, Mycological Research 97(8), pp. 1012-1014, 1993, Infection of grape flowers and berries by *Botrytis cinerea* . . . .
Newhook, NZ Journal of Science & Technology, vol. 38, Sec. A, Feb. 1957, pp. 473-481, The Relationship of Saprophytic . . . .
Reglinski et al, NZ Wine Grower Ann Res Supp 1996/97, p. 7, New Methods for Suppressing Powdery Mildew in Viticulture.
Reglinski et al, Proc of the 5th Annual Romeo Bragato Conf, 1999 7 pgs., Botrytis: Can we control it?
Reglinski et al, Durable Disease Resistance Syposium, 2000, Abstract SP42, Integrated use of an elicitor and a fungal . . . .
Schoene et al, Modern Fungicides & Antifungal Compounds II, 1998 Fungicide Sensitivity of Fungi used for Biocontrol of . . . .
Simmons, Mycologia, vol. 59, 1967, pp. 67-92, Typification of Alternaria, Stemphylium, and Ulocladium.
Vanneste et al, Intl Symp Buio Control Agents in Crop & Animal Protection, 1999, 2 pgs. Biological control of economically . . . .
Walter et al, Proc 11th Intl Botrytis Symp, 1996, p. 89, Selection of antagonistic saprophytes for suppression of . . . .
Wood, Annals Applied Biology 38, 1951, pp. 203-216, The Control of Diseases of Lettuc by the Use Antagonistic Organisms.
Zitter et al, Plant Disease, vol. 74, No. 10, 1990, pp. 824-827 A Leaf Spot of Cucumber Caused by *Ulocladium cucurbitae* in . . . .
Reglinski et al., New Zealand Wine Grower Ann. Res. Suppl., 1996/97, p. 7, Integrated use of an elicitor and a fungal antagonist to control Botrytis in grape.
Walter et al., 49th Proc. Of the New Zealand Pl. Prot. Conf., 1996, p. 316, Saprophytic suppression of *Botrytis cinerea* sporulation on kiwifruit leaf tissue.

* cited by examiner

*Primary Examiner*—Irene Marx
(74) *Attorney, Agent, or Firm*—Jacobson Holman PLLC

(57) ABSTRACT

The present invention relates to the use of *Ulocladium oudemansii* as a biological control agent. Processes and compositions for the biological control of *Botrytis* species using *Ulocladium oudemansii* are also provided.

12 Claims, 4 Drawing Sheets

BIOLOGICAL CONTROL OF PLANT DISEASES

FIELD OF THE INVENTION

This is a U.S. national phase application of PCT/NZ01/00111 filed Jun. 15, 2001 and publish in English.

BACKGROUND OF THE INVENTION

Plant disease caused by pathogens such as fungi are a significant economic cost to plant-based industries. Losses may arise through spoilage of produce both pre- and post-harvest, loss of plants themselves or through reduction in growth and fruiting abilities.

Traditionally, control of plant pathogens has been pursued through the application of chemicals such as fungicides. The use of chemicals is subject to a number of disadvantages. The pathogens can and have developed tolerance to chemicals over time, producing fungicide resistant populations. Chemical residues may also pose environmental hazards as well as raising health concerns.

The problem is particularly illustrated in the grape and wine industries. Bunch rot of grapes, caused by the fungus *Botrytis cinerea*, is estimated to cause losses of $18 million dollars per annum to the New Zealand wine industry alone. *Botrytis* control has been by way of fungicides. The practice is unsustainable because fungicide resistance is widespread in many vineyards and there is consumer pressure for reduction in pesticide residue.

Biological control presents an alternative means of controlling plant disease which is potentially more effective and specific than current methods, as well as reducing dependence on chemicals. Such biological control methods are perceived as a "natural" alternative to fungicides with the advantage of greater public acceptance, reduced environmental contamination and increased sustainability.

Mechanisms of biological control are diverse. One mechanism which has been demonstrated to be effective is the use of antagonist microorganisms such as bacteria, yeast and fungi to control plant disease.

Biological control of phytopathogenic fungi such as *Botrytis cinerea*, with selected biological control agents (BCAs) was reported by Wood in 1951 and later by Newhook in 1957 using the BCA fungus *Cladosporium cladosporiodes*. The introduction at that time of cheap, effective and easy to apply fungicides halted any further development of BCAs. More recently, other antagonistic microorganisms for use in biological control of plant disease have been identified.

The use of *Ulocladium atrum* to control *botrytis* in a range of plants has been proposed, for example for: *Botrytis* in onions (Köhl et al, 1995b), *botrytis* in lilies (Köhl et al, 1995a, Elmer & Köhl, 1998), *botrytis* in cyclamen (Köhl et al, 1998), and *botrytis* in grapes (Schoene et al, 1999). However, there are also reports of pathogenicity to some plant species exhibited by *U. atrum* (Butler et al. 1979).

The efficacy of various *Ulocladium* spp. such as *Ulocladium atrum* as biological control agents, has also been discussed by Elmer et al, 1995; Walter et al, 1996a,b; Boyd-Wilson et al, 1998; Reglinski et al, 1999, 2000, Hill et al, 1998, Vanneste et al, 1999, Michailides & Elmer, 2000.

It will therefore be appreciated that the *Ulocladium* species clearly considered as prime candidates for effective BCAs have been extensively researched over the past decade. However, to date none of the candidates have proved ideal, either due to plant pathogenicity concerns or through failure to quickly establish on the target plant plus survive the environmental variability existing in the field.

Surprisingly, the applicants have now identified a *Ulocladium* species not mentioned in any of the earlier reports as an effective BCA. The applicants have determined that this species, *Ulocladium oudemansii*, is highly effective in controlling saprophytic fungi such as *botrytis* and successfully establishing in plant tissues in the field. Moreover, to date there are no records of *U. oudemansii* causing disease in plants or plant products.

It is therefore an object of the present invention to provide a biological control composition comprising at least one strain of *Ulocladium oudemansii* effective against a *Botrytis* species, or at least to provide the public with a useful choice.

SUMMARY OF THE INVENTION

Accordingly, in one aspect, the present invention provides a biological control composition that comprises, in a reproductively viable form and amount, at least one strain of *Ulocladium oudemansii* effective against a *Botrytis* species and an agriculturally acceptable carrier, diluent or adjuvant.

Preferably, the at least one strain is present in the form of reproductively viable spores.

It is presently most preferred that the strain is, or the composition includes, *Ulocladium oudemansii* AGAL No. NM 99/06216.

The invention also provides a biologically pure culture of *Ulocladium oudemansii* AGAL No. NM99/06216.

In a further aspect, the present invention provides a process for controlling a *Botrytis* species in a plant or plant product, the process comprising applying a composition of the invention to said plant or plant product.

The invention further provides a process for controlling a *Botrytis* species in a plant or plant product, the process comprising applying an effective amount of at least one strain of *Ulocladium oudemansii* effective against a *Botrytis* species.

In a further aspect, the present invention relates to the use of *Ulocladium oudemansii* in a composition or process of the invention.

The invention also extends to the use of a composition of the invention for application to plants to control *botrytis* infection.

Plants treated with the composition of the invention also form a further aspect of the invention.

*rytis* levels in Chardonnay bunches at bunch closure during the season in Hawkes Bay. 10d, 20d, 30d, refers to the interval (in days) between NM99/06216 applications.

Figure 6:
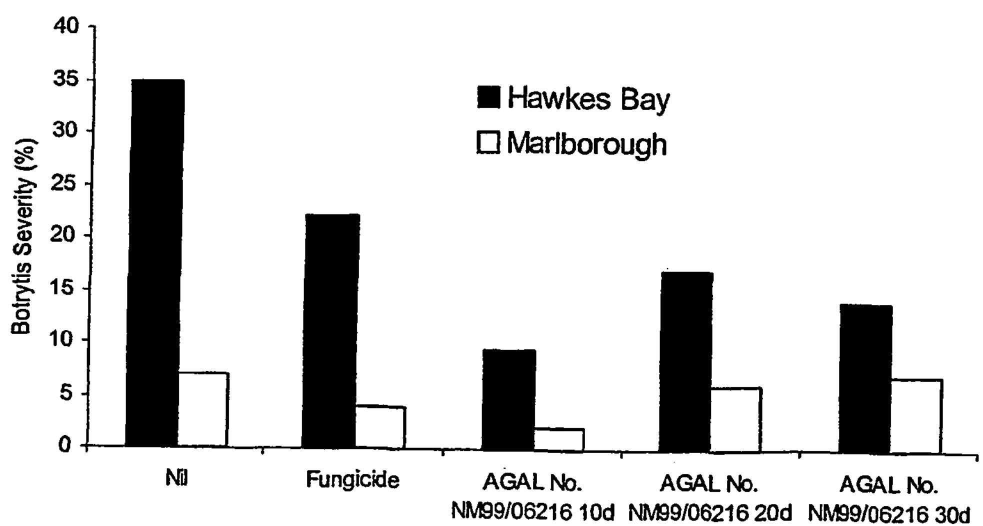

FIG. 6 is a bar graph depicting the effect of the frequency of biological control agent NM99/06216 applications on *Botrytis* levels in Chardonnay bunches at harvest in Hawkes Bay and Marlborough in 1999. 10d, 20d, 30d, refers to the interval (in days) between NM99/06216 applications.

Figure 7:
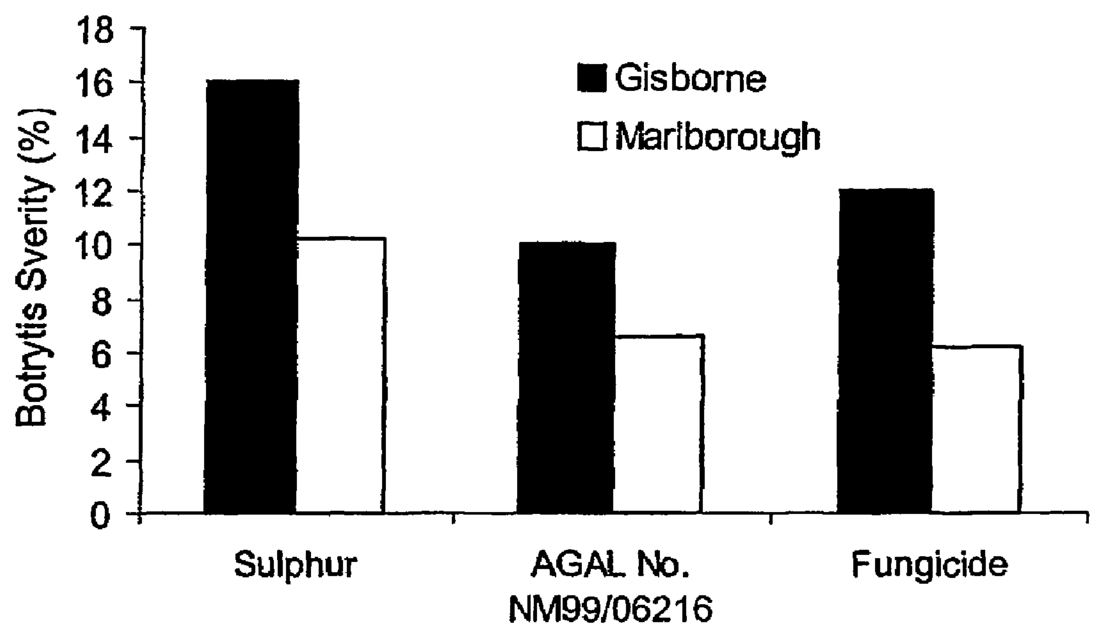

FIG. 7 is a bar graph depicting *Botrytis* levels on Merlot bunches (Gisborne), at harvest in and on Chardonnay bunches (Marlborough) after 48 h incubation in high humidity after harvest.

DETAILED DESCRIPTION OF THE INVENTION

The present invention is directed to strains of the *Ulocladium oudemansii* species having efficacy against *botrytis* and use thereof in controlling plant disease.

*U. oudemansii* is a saprophytic fungus which may be isolated from soil, wood, leaf, fruit or seeds. Isolates have the following identifying characteristics in comparison to *U. afrum* (Simmons, 1967):

| | Characteristics | | |
|---|---|---|---|
| *Ulocladium* sp | Mycelium | Conidiophores | Conidia |
| *U. atrum* | Ca. 5μ diameter, yellow to golden brown, smooth or sometimes minutely roughened | Up to 120 × 3-8μ, smooth or verrucose, golden brown | Golden brown or dark reddish brown, olivaceous, evenly and closely verrucose sometimes ellipsoidal or obovoid 15-32μ × 11-18μ with 1-3 transverse and 1 or more longitudinal septa **but predominantly with 2 complete oblique septa intersecting at right angles** but most commonly spherical or sub spherical |
| *U. oudemansii* | 3-6μ diameter Sub hyline to dilute yellow brown, **smooth** | Up to 250 × 5-8μ, golden brown smooth, bearing **solitary conidia.** | Initially **narrowly obovoid, hyline and smooth** becoming yellow brown and inconspicuously roughened: finally, broadly obovoid or ellipsoidal dark red brown to olivaceous Dimensions are 18-34μ × 11-17μ with 1-3 transverse and 1 or more longitudinal or oblique septa Apex is broadly rounded and often more **conspicuously verrucose than the remainder of the conidium which may be smooth** |

Text in bold are characteristics that may be used as a guide to distinguish between these two species, in addition to cultural characteristics and growth on HEA and PCA. described in Table 1.

Strains of *U. oudemansii* effective against *botrytis* and therefore suitable for use in accordance with the invention are identified as those which exhibit at least 50% antagonist efficacy expressed as a percentage reduction of the conidiophores of the relevant *Botrytis* species compared to the control treatment. By way of illustration, the methodology outlined in Example 3 below can be employed to identify *U. oudemansii* isolates effective against *B. cinerea*, whereas procedures analogous to those in Example 3 can be employed in relation to other *Botrytis* species.

One strain of *U. oudemansii* meeting the above requirements was isolated from kiwifruit leaf litter debris sampled from a kiwifruit research block at Massey University, Palmerston North, New Zealand, after incubation in high humidity chambers to induce saprophyte spore production. It demonstrates the high spore production typical of the genus when grown on oatmeal agar. Details of the isolation and selection process employed to obtain the isolate are set out in the Examples. This *Ulocladium. oudemansii* isolate has been deposited in the Australian Government Analytical Laboratories, (AGAL), 1 Suakin Street, Pymble, New South Wales, Australia on 2 September 1999 according to the Budapest Treaty for the purposes of patent procedure. The isolate has been accorded the deposit number NM 99/06216.

Accordingly, in one aspect the present invention provides a biologically pure culture of *U. oudemansii* AGAL No. NM 99/06216. Similarly provided are *Ulocladium* strains having the identifying characteristics of AGAL NO. NM 99/06216.

AGAL No. NM99/06216 and other isolates of *U. oudemansii* are particularly effective biological control agents, being capable of surviving interrupted wet periods, colonising necrotic tissues and suppressing *botrytis* growth and spore production in the field. The degree of suppression by these isolates of *U. oudemansii* is generally as good as the commonly used fungicide iprodione (Rovral™). Resistance (by *Botrytis cinerea*) to this particular fungicide has developed; in these and other instances, *Ulocladium oudemansii* isolates selected in accordance with the invention provide an effective alternative for *botrytis* control. This unexpected and potent activity in the control of plant disease coupled with the absence of any reports of plant pathogenicity induced by *U. oudemansii* demonstrate that isolates of the species have desirable attributes for use as a biological control agent.

The term "biological control agent" (BCA) as used herein refers to agents which act as antagonists of one or more phytopathogens. Antagonism may take a number of forms. In one form, the biological control agent may simply outcompete the pathogen for available nutrients and/or for space on the host plant. In another form, the biological control agent may render the environment unfavourable for the pathogen. Accordingly, the antagonist mechanisms include but are not limited to antibiosis, mycoparasitism, nutrient competition and physical displacement.

In a further aspect, the present invention provides a biological control composition comprising at least one strain of *U. oudemansii* effective against a *Botrytis* species and at least one agriculturally acceptable carrier, diluent or adjuvant. The composition may include multiple *U. oudemansii* strains, but preferably includes three strains or less, and most preferably a single strain. Suitably, the composition comprises isolate AGAL No. NM99/06216 as a single strain agent active against at least *Botiryis cinerea.*

Effective concentrations of *U. oudemansii* as biological control agent in the composition may vary depending on the end use, physiological condition of the plant; type, concentration and degree of pathogen infection; temperature, season, humidity, stage in the growing season and the age of plant; number and type of conventional fungicides being applied; and plant treatments (such as leaf plucking and pruning) may all be taken into account in formulating the composition.

The strain of *U. oudemansii* included as biological control agent must be in a reproductively viable form. For most purposes, the *U. oudemansii* is desirably incorporated into the composition in the form of spores. The concentration of the fungal spores in the composition will depend on the utility to which the composition is to be put. An exemplary concentration range is from about $1\times10^2$ to $1\times10^7$ spores per ml, preferably from about $1\times10^3$ to $2\times10^6$, and more preferably for *U. oudemansii* $1\times10^4$ to $2\times10^6$ spores per ml.

It is anticipated that using conventional static dry and liquid fermentation technology, *U. oudemansii* spores from selected strains can be produced in bulk for field application. Growth is generally effected under aerobic conditions at any temperature satisfactory for growth of the organism. A temperature range of from 8 to 30° C., preferably 15 to 25° C., and most preferably 20° C. is preferred. The pH of the growth medium is slightly acid to neutral, that is about 5.0 to 7.0, and most preferably 6.0. Incubation time is sufficient for the isolate to reach a stationary growth phase, about 3 to 4 weeks when incubated at 18° C., and will occur in the dark. The spores may be harvested by conventional filtering or sedimentary methodology (eg. centrifugation) or harvested dry using a cyclone system. Spores can be used immediately or stored, chilled at 1° to 7° C., preferably 2° C., for as long as they remain reproductively viable. It is however generally preferred that use occur within two weeks of harvesting.

The composition of the invention may also include agriculturally acceptable carriers, diluents or adjuvants. The compositions may also comprise a broad range of additives such as surfactants, wetters, humectants, stickers, spreaders, stablisers and penetrants used to enhance the active ingredients and so called 'stressing' additives to improve spore vigor, germination and survivability such as potassium chloride, glycerol, sodium chloride and glucose. Additives may also include compositions which assist in maintaining microorganism viability in long term storage, for example unrefined corn oil and so called invert emulsions containing a mixture of oils and waxes on the outside and water, sodium alginate and conidia on the inside.

Examples of surfactants, spreaders and stickers include Fortune®, Pulse, C-Daxoil®, Codacide oil®, D-C. Tate®, Supamet Oil, Bond® Penetrant, Citowett® and Freeway.

Examples of suitable compositions including carriers, preservations, surfactants and wetting agents, spreaders, and nutrients are provided in U.S. Pat. No. 5,780,023 incorporated herein by reference.

Where selected for inclusion, common agricultural surfactants, such as TWEEN® (polysorbate surfactant (available from Rohm & Haas) are desirably included in the composition according to known protocols. It is important that any additives used are present in amounts that do not interfere with the effectiveness of the biological control agents.

The applicants have also determined that many commonly used fungicides do not adversely affect *U. oudemansii*. The compositions of the invention may therefore also include such fungicides. Alternatively, the compositions may be used separately but in conjunction with such fungicides in control programmes.

The compositions may be prepared in a number of forms. One preparation comprises a powdered form of composition of the invention which may be dusted on. In a further form, the composition is mixed with a diluent such as water to form a spray, foam, gel or dip and applied appropriately using known protocols. In the presently preferred embodiment, the *U. oudemansii* composition is applied in 0.1% v/v TWEEN®80 (polyoxyethylenesorbitan monooleate) mixed with water using a pressurised sprayer.

Compositions formulated for other methods of application such as injection, rubbing or brushing, may also be used, as indeed may any known art method. Indirect applications of the composition to the plant environment such as soil, water, or as seed coatings are potentially possible.

In a further aspect, the present invention provides a process for controlling *botrytis* in a plant, the process comprising applying at least one strain of *U. oudemansii* effective against a *Botrytis* species, or a composition of the invention to said plant.

The term "controlling" as used herein generally comprehends preventing or reducing *botrytis* infection or inhibiting the rate and extent of such infection. Curative treatment is also contemplated.

Again, while multiple strains of *U. ouedemansii* with activity against a *Botrytis* species may be employed in the control process, preferably three strains or less, and more preferably a single strain is used in the process. In the presently most preferred embodiment, the single strain *U. oudemansii* AGAL No. NM99/06216 is employed.

Repeated applications at the same or different times in a crop cycle is also contemplated. The *U. oudemansii* may be applied either earlier or later in the season. This may be over flowering. The *U. oudemansii* may also be applied immediately after harvest to rapidly colonise necrotic or senescing leaves and machine harvested stalks (rachides) to prevent *Botrytis* colonisation, particularly of *Botrytis cinerea* on grape leaves and stalks. The *U. oudemansii* may also be applied to dormant grape vines in winter to slow *Botrytis* growth in dormant tissues.

Application may be at a time before or after bud burst and before and after harvest. However, treatment preferably occurs between flowering and harvest. To increase efficacy, multiple applications (for example, 2 to 6 applications over the phenological stages of flowering through fruiting, or bunch closure for grapes) of the *U. oudemansii* or a composition of the invention is preferred.

Reapplication of the *U. oudemansii* or composition should also be considered after rain. Using *Botrytis* prediction models, application of the BCA can also be timed to account for *Botrytis* risk periods.

In the presently preferred embodiments, the *U. oudemansii* is applied in a 0.1% v/v TWEEN®80 (polyoxyethylenesorbitan monooleate) solution using a pressurised sprayer. The plant parts should be lightly sprayed until just before run off. Applications may be made to either the whole plant canopy or just to the area in the canopy where the flowers and developing fruit are concentrated (e.g. "bunchline" in grapes).

The applied compositions control *botrytis. Botrytis* spp. is responsible for many of the pre- and post-harvest molds which attack plant parts and cause grey mold in grapes and kiwifruit, glasshouse crops, process tomatoes, stonefruits, cut flowers, strawberries, and ornamental plants as well as a plethora of other plants. In one embodiment, the compositions of the present invention are therefore, desirably formulated for use against one or more of *Botrytis cinerea* and/or *Botrytis fabae, Botrytis aclada* and *Botrytis elliptica*) *Botrytis squamosa, Botrytis allii*. Control of *Botrytis cinerea* in grape using the compositions and method of the present invention is particularly contemplated.

The term "plant" as used herein encompasses not only whole plants, but extends to plant parts, cuttings as well as plant products including roots, leaves, flowers, seeds, stems, callus tissue, nuts and fruit. Plants that may benefit from the application of the present invention cover a broad range of agricultural and horticultural crops. The compositions of the present invention are also especially suitable for application in organic production systems.

The process of the invention has particular application to plants and plant products, either pre- or post-harvest. For example, the composition of the invention may be applied to stored products of the type listed above including fruits, vegetables, cut flowers and seeds. Suitable application techniques encompass those identified above, particularly spraying.

The composition can potentially be used to treat or pretreat soils or seeds, as opposed to direct plant application. The composition may find use in plant processing materials such as protective coatings, boxes and wrappers.

Also encompassed by the present invention are plants, plant products, soils and seeds treated directly with an active strain of *U. oudemansii* or a composition of the invention.

In a further aspect, the present invention extends to the *Ulocladium oudemansii* of the invention for use in a composition of the invention.

The following non-limiting examples are provided to illustrate the present invention and in no way limit the scope thereof.

EXAMPLE 1

*Ulocladium oudemansii* (AGAL No. NM 99/06216)

This was originally isolated from kiwifruit leaf litter sourced from the Massey University kiwifruit research orchard at Palmerston North. The leaf litter sample was incubated in a high humidity chamber to encourage spore production by saprophytic fungi. Conidia belonging to *Ulocladium* spp., from the leaf litter sample, were cultured onto oatmeal agar for purification of the culture and later testing according to the protocol of Example 3.

*Ulocladium* Characteristics

The isolate was identified as *Ulocladium oudemansii* at the Centraalbureau voor Schimmelcultures (CBS), Delft, The Netherlands using the taxonomic reference of Simmons, E G (1967).

Morphological Characteristics

*Mycelium* pale olivaceous-brown, smooth or minutely roughened. Colonies on agar (Potato carrot agar, PCA) growing rapidly, velvety black or olivaceous charcoal-black with a white margin. After 9 days at 20° C., the culture diameter is 72 mm. On oatmeal agar (OA) colonies first appear brown (1-2 days) then appear olivaceous for the first 2-7 days, then progressively become darker so that the entire colony has a black velvety appearance after 3-4 weeks. Colony growth is rapid so that the entire petri dish (90 mm diameter) is covered after 12 days in the dark at 18° C. On PDA (potato dextrose agar), colony growth is slower, and the culture takes on a more dark olivaceous-slate grey appearance. On this medium the entire petri dish (90 mm diameter) is covered after 14-16 days in the dark at 18° C. On hay extract agar (HEA) growth was 40 mm after 10 days at 10° C. and continuous UV light. The colony was characterised by being more lobulate. The growth characteristics, colony and conidial morphology of AGAL No. NM 99/06216 on HEA may be a useful discriminating characteristic as summarised below.

Colony and conidial characteristics of related *Ulocladium* spp. isolates grown at 10° C. with continuous UV light on hay extract agar are outlined in Table 1.

TABLE 1

| | | Colony diameter on: | | | Degree of |
|---|---|---|---|---|---|
| Isolate | *Ulocladium* sp. | PCA (9 days) | HEA (10 days) | Conidia carried on; | "warts" on conidia |
| AGAL No. NM 99/06216 | *Ulocladium oudemansii* | 72 mm | 40 mm | Short chains | Few warts |
| HRU G | *Ulocladium oudemansii* | 80 mm | 78 mm | No chains | Coarsely warted |
| HRV N | *Ulocladium oudemansii* | >85 mm | 68 mm | No chains | Few warts |
| U385 | *Ulocladium atrum* | 70 mm | 50 mm | No chains | Distinctly warted |

Conidial Morphology of *Ulocladium oudemansii*

Conidiophores are abundant, erect or ascending, simple or branched, golden brown, smooth, setate, bearing solitary conidia at 1-5 uniportate geniculations. Conidia are initially narrowly obovoid, hyline, smooth, becoming yellowish brown, and inconspicuously roughened; finally broadly obovoid or ellipsoidal, dark olivaceous-charcoal 21.6-30.8 by 10.8-16.9 microns with 1 or 3-5 transverse and one or two longitudinal or oblique septa, base broadly conical to rounded, apex broadly rounded and often more conspicuously verrucose (warted) than remainder of conidium. Conidia germinate readily on moist substrates producing one or more rapidly growing hyphae per conidium.

Recipes for PCA (Potato Carrot Agar), HEA (Hay Extract Agar), PDA (Potato Dextrose Agar) and OA (Oatmeal Agar) used in the above tests were prepared according to Gams et al. 1998.

EXAMPLE 2

Preparation of *Ulocladium oudemansii* for Field Experiments

Storage cultures of *U. oudemansii* (including AGAL No. NM 99/06216), were preserved in 15% sterile glycerol at −70° C. and stored until required.

The *U. oudemansii* isolates were grown on oatmeal agar (OA) slant cultures in 35-50 ml testtubes with a cotton wool bung, for 2-3 weeks at 180° C. in the dark. 10-20 ml of sterile MILLIPURE™ water (plus 0.0 1% TWEEN®80 (polyoxyethylenesorbitan monooleate) was added to the slant cultures which were then gently scraped with a sterile scalpel to dislodge conidia. For small fermentation runs, the resultant spore suspension was then added to whole moistened organic oats (autoclaved twice for 45 minutes at 12° C., 100 kPa) in sterile culture bags (Type MBO3LPP, Van Leer flexible packaging, Pont-Audemer, France). These culture bags were then sealed with adhesive tape and incubated at 18° C. in the dark for 3-4 weeks.

The *U. oudemansii* isolates were prepared for field experiments using the following protocol. All colonized oats were removed from the culture bags and placed into a nylon mesh bag in a spore washing device (Miniwash 2000SR MW100, Piraeus, Greece). Chilled MILLIPURE™ water (plus 0.0 1% TWEEN®80 (polyoxyethylenesorbitan monooleate) was added and the colonized oats thoroughly washed in this device for 30 minutes. The resultant suspension was passed through a primary filter (mesh=4 mm×4 mm) to remove whole oats and then a secondary filter consisting of fine sterile nylon gauze (mesh200 μm) to remove small particles and mycelial fragments. The concentration of this suspension was determined with the aid of a haemocytometer and adjusted to $2\times10^6$ conidia $m^{-1}$ with chilled MILLIPURE™ water (plus 0.01% TWEEN®80 (polyoxyethylenesorbitan monooleate) and kept on ice at 5° C. for a maximum of 2 weeks before use in the field. Our studies have shown that storage at this temperature for this length of time did not result in a reduction of spore viability or subsequent germ tube vigor. The isolate suspension was applied to prelabelled grape (cv Chardonnay) bunches using 4L Yates MaxiSpray pneumatic sprayers.

EXAMPLE 3

Process for Selection of Biological Control Agents

Introduction

Effective biological control agents can be selected according to their ability to displace or exclude a potential disease-causing microorganism from its substrate or ecological niche. Under conducive conditions phytopathogens such as *Botrytis cinerea* may colonise senescent dead or necrotic tissue. Competitive, non-pathogenic saprophytes may be applied so as to exclude and/or out-compete the phytopathogen, thereby preventing or limiting the disease-causing capability of the pathogen. The effectiveness of these saprophytes in the field is in turn dependent on their ability to survive varying climatic conditions, such as interrupted wet periods and desiccation. A method is provided by which competitive saprophytes with these characteristics may be selected. The method follows that originally devised by Dr Jurgen Köhl for onion and lily leaves (Köhl et al, 1995a, 1995b).

Methods

Discs (dia. 21 mm) were cut from mature unsprayed grape or kiwifruit leaves selected at random and placed between sheets of cardboard. The discs were gently dried at 40° C. for approximately 9 hours and then washed under running water for 10 minutes to remove any soluble nutrients. The leaf discs were then blot dried once more on sterile paper towels, dried at 40° C. for 6 hours, then sealed in plastic specimen jars, prior to sterilization by gamma-irradiation (4Mrad).

Isolates of saprophytic fungi such as *Ulocladium* spp. may be readily isolated from soil, wood, leaf, fruit or seed surfaces as reported in Example 1.

Isolates were maintained on oatmeal agar (30 g finely ground oatmeal plus 20 g agar per litre of water) and incubated for 2 to 4 weeks at 20° C. illuminated according to a 12 hours day/night cycle. Fungal propagules were washed from the sporulating agar plates using sterile 0.01% (v/v) TWEEN®80 (polyoxyethylenesorbitan monooleate) in distilled water. The spore suspensions were filtered through sterile lens tissue (Whatman) to remove mycelial fragments and centrifuged at 4000 rpm for 2 min. The supernatant was carefully decanted from the spore pellet and the spores resuspended in fresh sterile 0.01% (v/v) TWEEN®80 (polyoxyethylenesorbitan monooleate) in distilled water. The centrifuging and washing procedure was repeated and the final spore density adjusted to $1\times10^6$ conidia $m^{-1}$ with the aid of a haemocytometer.

Sterile leaf discs (4) were placed in a high humidity chamber which consisted of a sterile plastic petri dish (90 mm diameter) containing 2 sterile filter papers (Whatman), moistened with 2 mL sterile distilled water (SDW). Leaf discs were refrigerated (4° C.) overnight to allow the tissue to imbibe the applied water. Following rehydration, leaf discs were inoculated with a conidial suspension of *Botrytis cinerea* ($1\times10^4$ spores/$ml^{-1}$) and incubated in the high humidity chambers for 8 hours at 18° C. in the dark. After this incubation period, isolates of candidate BCAs (saprophytes) were applied to the *B. cinerea* inoculated leaf discs, by misting a fine suspension ($1\times10^6$ spores/$ml^{-1}$) onto the leaf disks in the humidity chambers. Co-inoculated tissues were then incubated in the high humidity chambers for a further 16 hours at 18° C. in the dark.

High humidity incubation was interrupted by transferring the leaf disks from the humidity chambers to open petri dishes containing 2 layers of sterile dry (Whatman) filter disks. Leaf disks were then air dried in a laminar flow cabinet for 6 hours at 20-22° C. After this period of stimulated desiccation the tissues were rehydrated, by applying 2 mL SDW, then sealed in the humidity chamber and incubated for 10 days at 18° C. in the dark. The area of leaf disk tissue with *B. cinerea* sporulation was assessed visually. Controls were employed; rehydrated leaf discs with nil inoculum, rehydrated leaf discs with *B. cinerea* inoculum only.

Statistical Analysis

Prior to analysis of variance, all data were arcsin transformed using an angular transformation to stabilise the variance and LSD values were calculated for purposes of mean separation Results Many isolates performed significantly better than the conventional fungicide with 90-100% suppression of *B. cinerea* sporulation being achieved. The better performing isolates were selected for a repeat laboratory bioassay to confirm *B. cinerea* suppression. Results of the repeat bioassay for *Ulocladium* spp. only are presented in Table 2. The best performing isolates were selected for further field evaluation and confirmation of the repeat lab bioassays as outlined in Example 4.

TABLE 2

Suppression of *B. cinerea* sporulation by *Ulocladium* spp. on necrotic kiwifruit leaf tissues with an interrupted wet period in a repeat bioassay to confirm antagonist efficacy.

| Treatment | % coverage of necrotic leaf tissue by *B. cinerea* conidiophores | |
|---|---|---|
| *B. cinerea* control | 25 | |
| *Ulocladium* spp. | | |
| *U. oudemansii* (AGAL No. NM 99/06216] | 6 | 76[a] |
| *U. atrum* [U385 Dutch isolate) | 11 | 56 |
| Fungicide (iprodione) | 20 | 20 |
| LSD (P < 0.05) | 5.6 | |

[a]Antagonist efficacy, expressed as a percentage reduction of *B. cinerea* conidiophores compared to the *B. cinerea* control treatment.

EXAMPLE 4

For field testing of *U. oudemansii* (AGAL No. NM99/06216) rehydrated necrotic kiwifruit leaf discs were placed onto small strips of plastic Coreflute™ (Waikato Signs, Hamilton, New Zealand) (5 discs per strip) and inoculated with *B. cinerea* as described above for the laboratory based trials, then transferred to the crop canopy without rehydration for incubation for 22 hours under field conditions. Pathogen inoculated leaf discs were returned to the lab, inoculated with AGAL No. NM99/06216 as described above for the laboratory based trials, then returned to the field and suspended in the crop canopy. All treatments were randomised with regard to position in the canopy. Once again control treatments were included; leaf discs with nil inoculum, leaf discs with *B. cinerea* inoculum only. No pesticide treatments were applied by the farmer during the incubation period of 10 days. Following incubation under field conditions leaf discs were collected from the crop canopy and incubated in high humidity chambers for 10 days as described above for the lab tests. Disks were assessed for *B. cinerea* spore production as described before. This field screening procedure was repeated 11 times to ensure exposure to a wide range of environmental conditions.

Results

Figure 1:
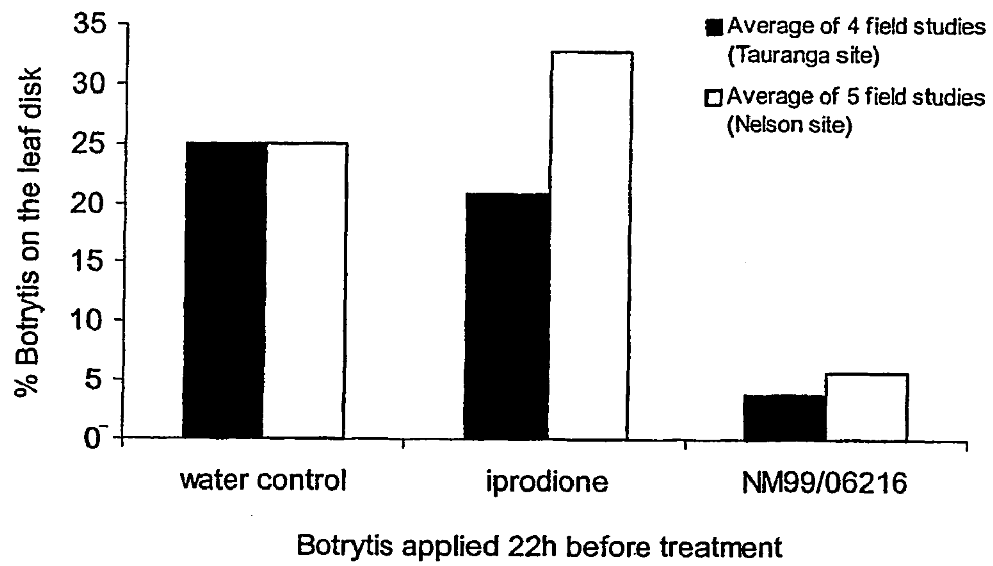
FIG. 1 is a bar graph comparing the efficacy of *Ulocladium oudemansii* isolate (AGAL No. NM99/06216) on suppression of *botrytis* development with the fungicide iprodione.

The AGAL No. NM99/06216 isolate performed significantly better than the conventional fungicide, iprodione (Rovral®) in up to 11 repeated field tests. The isolate consistently and repeatedly reduced *Botrytis cinerea* sporulation by 80-100% (see FIG. 1), even when *B. cinerea* was applied 22 h before the isolate was applied.

Discussion

The AGAL No. NM99/06216 isolate effectively suppresses *B. cinerea* growth and sporulation in all these assays.

EXAMPLE 5

Materials and Methods

Field Trial

Field studies commenced in a block of Chardonnay with a history of *Botrytis cinerea*, at Montana's Twin Rivers site (Taradale, Napier, New Zealand). Eight treatments (see below) were selected and applied to single vine plots (eight labelled bunches per vine) in each of 5 replicate rows (40 bunches per treatment in total). There were buffer rows on each side of the treated area.

Treatments

1) Untreated
2) Pulse (0.1%)
3) TWEEN® (polysorbate surfactant) (0.05%)
4) Algan (0.5%; plus Pulse)
5) AGAL No. NM99/06216 spray (plus TWEEN® (polysorbate surfactant)
6) AGAL No. NM99/06216 Dipped (plus TWEEN® (polysorbate surfactant)
7) Lemongrass oil (0.1%; plus Pulse)
8) Shirlan (1 ml/L)

AGAL No. NM99/06216 spore suspension adjusted to $2\times10^6$ spores/ml

Application

Treatments were applied through summer and early autumn on December 15, December 23, December 30, January 13, January 28, February 12, February 24, March 6, March 16, March 26, April 9. Treatments were applied to run-off using hand held pneumatic sprayers with the exception of treatment 6 which was applied by dipping the bunches.

Harvest

*Botrytis* incidence at commercial harvest was very low. The harvest of this trial was delayed for two weeks to encourage further *botrytis* development. On April 21 the labelled bunches were harvested, placed in polythene bags on ice and then transported to HortResearch laboratories at Ruakura Research Centre. Bunches were removed from the polythene bags and bunch rot was estimated by counting the number of berries in each bunch that were infected with *botrytis.*

High Humidity Incubation Test

In order to promote *botrytis* development, after the harvest assessment each grape bunch was placed into a plastic container (Plix Packaging, Carter Holt Harvey, New Zealand) with moistened paper towels in the base of each container to maintain a humid environment. The containers were randomised and incubated at 20° C.+/−2° C. The second bunch rot assessment was carried out after 2 days incubation. The bunches were left to incubate in high humidity for a further 12 days in order to test the treatments under severe conditions. After this period *botrytis* infection levels were very high and bunch rot was measured using the following scale:

| Bunch Severity Score | % bunch infection |
|---|---|
| 0 | 0 |
| 1 | 1-10 |
| 2 | 11-25 |
| 3 | 26-50 |
| 4 | 51-75 |
| 5 | 76-100 |

Statistical Analysis

Before analysis of variance the data were transformed using an angular transformation to stabilise the variance. An analysis of the raw data gave similar conclusions to those of the analysis after transformation, and therefore the raw data have been presented for simplicity.

Results

Field Observations

None of the treatments caused any visible damage to the grape bunches. The vines were examined at regular intervals for the presence of *botrytis* and disease incidence was very low. Hence, the harvest was delayed until April 21 to favour *botrytis* development in the trial block.

*Botrytis* Assessment at Harvest

Figure 2:
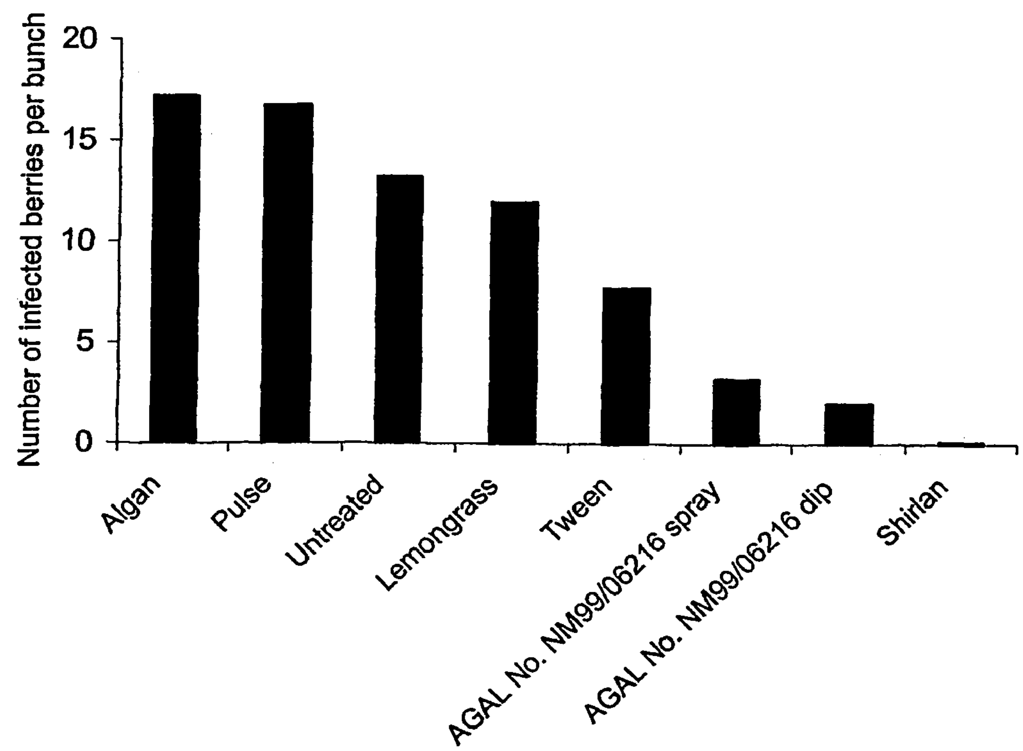
FIG. 2 is a bar graph depicting the level of *botrytis* infection in grape bunches at harvest. The asterisk (*) denotes bunches showing significantly different levels of *botrytis* infection compared with the untreated control at $P<0.05$.

Although botrytis levels were low at harvest there were significant treatment effects. The untreated bunches and those treated with Algan, Lemongrass oil, Pulse and TWEEN® (polysorbate surfactant) had between 7-17 infected berries per bunch (approximately 5-10% infection) (FIG. 2). All other treatments had significantly (P<0.05) lower levels of botrytis (<2% infection).

Figure 3:
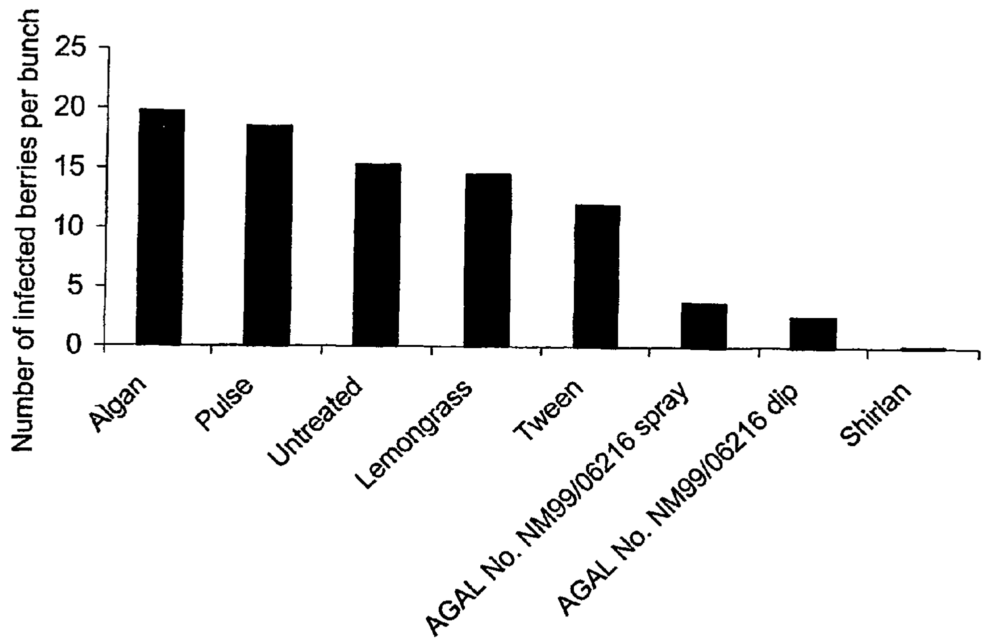
FIG. 3 is a bar graph depicting the level of *botrytis* infection in the same grape bunches after two days incubation in high humidity (conditions conducive to disease development). The asterisk (*) denotes bunches showing significantly different levels of *botrytis* infection compared with the untreated control at $P<0.05$.

Botrytis Development on Bunches After 2 Days Incubation in High Humidity Chambers There was a general increase in *botrytis* on bunches following 2 days incubation in high humidity chambers. However, infection level on bunches treated with AGAL No. NM 99/06216 (sprayed or dipped) and Shirlan remained significantly (P<0.05) lower than the untreated control (FIG. 3).

*Botrytis* Development on Bunches After 14 Days Incubation in High Humidity Chambers

Figure 4:
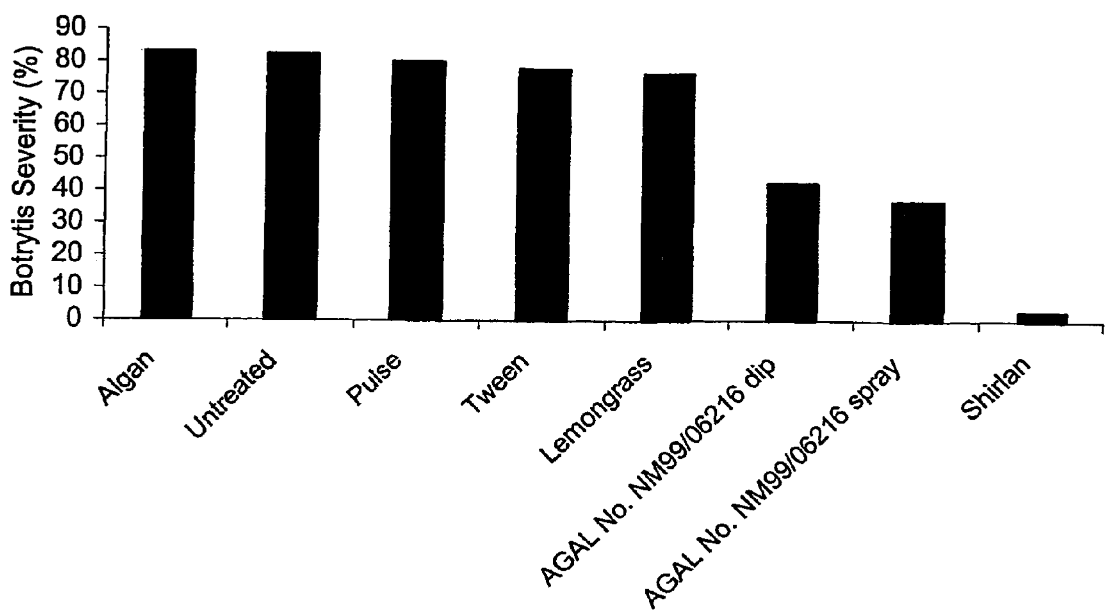
FIG. 4 is a bar graph depicting the level of *botrytis* infection in the same grape bunches after fourteen (14) days incubation in high humidity (conditions conducive to disease development).

*Botrytis* infection levels ranged from 75 to 83% on untreated bunches and those treated with Pulse, TWEEN® (polysorbate surfactant), Algan and lemongrass oil. On bunches treated with AGAL No. NM99/06216 (sprayed and dipped) the level of infection was between 36-41%. The most effective treatment was SHIRLAN® where botrytis incidence was 3% (FIG. 4). However this level of control was achieved by making 12 applications of SHIRLAN® during the season, something well outside normal commercial practice. In the vineyard, SHIRLAN® use would be restricted close to harvest to avoid potential residue problems and one would expect to use only half this number of applications.

Discussion

Selected elicitors, antagonists and antimicrobial natural products were evaluated for *botrytis* control in grapes (cv. Chardonnay) at the Twin Rivers vineyard in Napier. There were significant reductions of *Botrytis cinerea* on bunches treated with AGAL No. NM99/06216 isolate and the fungicide Shirlan when compared to the untreated controls at harvest. Bunches were then incubated in high humidity conditions to favour *botrytis* development. After 14 days incubation, *botrytis* levels were still significantly lower on bunches treated with the isolate and Shirlan compared to the untreated controls. Lemongrass oil, Algan and the wetting agents Pulse and Tween did not control *botrytis.*

This is a practical demonstration of the use of a biological control agent to control *botrytis* in viticulture in the field. This excellent result indicates the potential of biological control.

EXAMPLE 6

Introduction

The purpose of this study, was to confirm the findings described above in Example 5 and to extend the scope of the investigation. Field trials were carried out in two major grape growing regions of New Zealand, Hawkes Bay and Marlborough, to determine the potential impact of regional and seasonal variation on biological control treatment efficacy. The results and conclusion of this study are presented.

Methods

Trial Sites

Field trials were set up at Hawkes Bay and Marlborough. Treatments (Table 3) were applied to each of 10 labeled bunches per vine in single vine plots (cv. Chardonnay) using Yates Plassay Maxi4 pressure sprayers. There were 5 replicate vines per treatment with untreated buffer vines between each treated vine and untreated buffer rows on each side of the trial block area to provide sufficient *B. cinerea* inoculum for infection of flowers and fruit.

TABLE 3

Treatments for 1998/99 field trials
1998/99 Vineyard Trials

| Treatment | Spray Programme | Site |
|---|---|---|
| AGAL No. NM99/06216 | every 10, 20 and 30 days | Hawkes Bay & Marlborough |
| Wetter only (Pulse) | every 10 days | Hawkes Bay & Marlborough |
| Fungicide | Conventional spray Programme* | Hawkes Bay & Marlborough |

*U. oudemansii* suspensions contained $2 \times 10^6$ conidia $ml^{-1}$ in 0.01% (v/v) TWEEN ® (polysorbate surfactant).
*The conventional spray programme consists of consisted of SWITCH ®, and SHIRLAN ® (Hawkes Bay) or EUPAREN ® DF (Marlborough) applied during capfall; Crop Care Captan WG applied pre-bunch closure and at veraison; and ROVRAL ® Flo applied twice pre-harvest (Hawkes Bay only).

*U. oudemansit* suspensions contained $2\times10^6$ conidia $ml^{-1}$ in 0.01%(v/v) TWEEN® (polysorbate surfactant).

*The conventional spray programme consists of consisted of SWITCH®, and SHIRLAN®(Hawkes Bay) or EUPAREN® DF (Marlborough) applied during capfall; Crop Care Captan WG applied pre-bunch closure and at veraison; and ROVRAL® Flo applied twice pre-harvest (Hawkes Bay only).

The first treatments were applied early November at Hawkes Bay and late November at Marlborough. Thereafter, applications (except fungicides which were applied according to the conventional or industry standard BOTRYTIS spray programme), were made every 10, 20 or 30 days.

Disease Assessment

Pre-labeled bunches were visually monitored throughout the season for any signs of phytotoxicity and for the incidence of *botrytis*. Disease assessments were carried out at Hawkes Bay late January and at both sites in mid-March. On each date the number of *botrytis* infected berries per bunch was recorded. *Botrytis* incidence was low at Marlborough and so bunches were removed from the vine, incubated for 48 h under conditions favourable for *botrytis* development, then assessed. Statistical analysis of results was performed using ANOVA. Before analysis of variance the data were transformed using an angular transformation to stabilise the variance. Analysis of the raw data gave similar conclusions to those of the analysis after transformation, and for simplicity we have presented the raw data.

Results

Mid-Season Assessment at Hawkes Bay

None of the treatments caused any observable damage to grape tissues at any stage of the season at the Hawkes Bay site. Heavy rainfall during January in Hawkes Bay was followed by the development of *botrytis* in the trial block. Profuse *botrytis* sporulation was observed on untreated bunches both in the untreated buffer vines and the untreated bunches in the plots, indicating that abundant *botrytis* inoculum was available for infection at that time.

Figure 5:
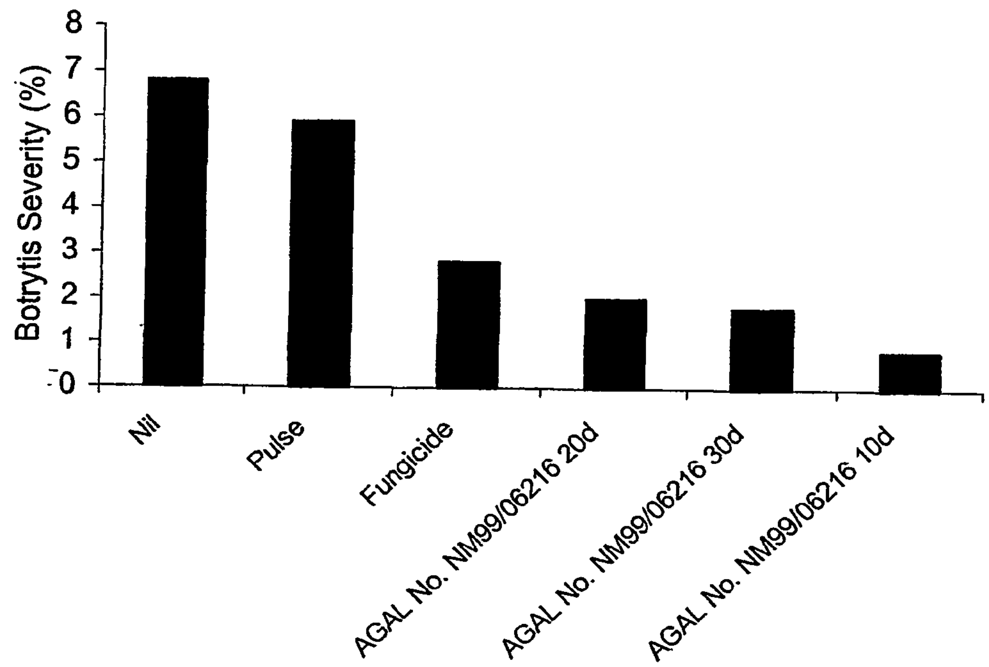
FIG. 5 is a bar graph depicting the effect of the frequency of biological control agent NM99/06216 applications on *Bot-*

Bunches on the untreated vines had the highest level of *botrytis* with approximately 7 infected berries per bunch (FIG. 5). All treatments with the exception of the wetter control "Pulse" significantly reduced *botrytis* incidence. The "10 day" *U. oudemansii* AGAL No. NM99/06216 treatment reduced *botrytis* by over 80% and the "20 day" and "30 day" treatments by ca. 70%. This compared favorably with the conventional fungicide programme which reduced *botrytis* incidence by approximately 60%. There was no evidence of *botrytis* infections at the Marlborough site at this time.

*Botrytis* Assessment at Harvest

Confirming Efficacy of *Ulocladium oudemansii*

*Botrytis* severity at Hawkes Bay was highest on the untreated bunches with an average of 35 infected berries per bunch. The *U. oudemansii* AGAL No. NM99/06216 treatments were at least as effective as the fungicide. These results confirm our earlier findings described in example 5 above.

Effect of Regional Variation and Time Interval on *U. oudemansii* AGAL No. NM99/06216 Efficacy

*Botrytis* severity was generally lower in Marlborough than in Hawkes Bay (FIG. 6). As the time interval between applications of *U. oudemansii* AGAL No. NM99/06216 was extended from every 10 to every 20, or every 30 days, there was a reduction in treatment efficacy. However, the level of disease control in all treatments still compared favorably with the conventional fungicide program in Hawkes Bay. In Marlborough, where there was minimal disease pressure, results were less clear-cut. *Botrytis* incidence in all Marlborough treatments, including the non-treated control, was less than 8%.

Discussion

*Ulocladium oudemansii* AGAL No. NM99/06216 was evaluated for *botrytis* control in grapes (cv. Chardonnay) at vineyards in Hawkes Bay and Marlborough. All of the *U. oudemansii* treatments were as effective as the fungicide, and in some cases significantly better. These results confirm our earlier findings, as reported in example 5, and the result for Hawkes Bay was especially encouraging considering that we placed very high inoculum pressure on the treatments (adjacent buffer vines and the majority of bunches in the vine were untreated).

Spraying every 10 days could add up to as many as 15 applications during a season and this may be undesirable for growers. Increasing the treatment interval to 20 or 30 days resulted in a reduction in efficacy, but still provided a level of disease control equivalent to that obtained with a conventional fungicide program. Another way of reducing fungicide applications might be to target particular growth stages. Work on other crops and with other chemicals has demonstrated that early season suppression of *botrytis* is important in effective disease control (Nair & Allen, 1993). We explore this approach in Example 7.

EXAMPLE 7

Introduction

The purpose of this study was to further extend the work undertaken in Example 6 and examine the effect of targeting applications on *botrytis* control. Once again field trials were carried out in two major grape growing regions of New Zealand, Gisborne and Marlborough to take into account regional and seasonal variation on treatment efficacy. The results and conclusion of this study are presented.

Methods

Trial Sites

Similar field trials were set up at Gisborne and Marlborough. Treatments (Table 4) were applied to each treatment plot of 3 vines (cv. Chardonnay in Blenheim and cv. Merlot in Gisbome) using 15 litre "Solo" backpack sprayers. There were 5 replicate plots per treatment with untreated buffer vines on either side of each treated group of vines and untreated buffer rows on each side of the trial block area to provide sufficient *B. cinerea* inoculum.

TABLE 4

| Treatments | | |
|---|---|---|
| Treatment | Spray Programme | Site |
| No botryticides | Sulphur applied to keep powdery mildew under control[1] | Gisborne & Marlborough |
| *U. oudemansii* AGAL No. NM99/06216 | At flowering, bunch closure and veraison | Gisborne & Marlborough |
| Standard Fungicide | Industry standard spray Programme* | Gisborne & Marlborough |

[1]Sulphur is not known to have any effect on Botrytis control
[2]NM99/06216 suspensions contained 2 × 106 conidia ml−1 in 0.01% TWEEN ®80 (polyoxyethylenesorbitan monooleate).
[3]The industry standard spray programme used to control botrytis was SWITCH ®, and EUPAREN ® DF applied during capfall; with Crop Care Captan WG applied pre-bunch closure and at veraison (two sprays at veraison in Gisborne);

1. Sulphur is not known to have any effect on *Botrytis* control
2. NM99/06216 suspensions contained 2×106 conidia ml-1 in 0.01% TWEEN®80 (polyoxyethylenesorbitan monooleate).
3. The industry standard spray programme used to control *botrytis* was SWITCH®, and EUPAREN® DF applied during capfall; with Crop Care Captan WG applied pre-bunch closure and at veraison (two sprays at veraison in Gisborne);

Except for the industry standard fungicide programme, the first treatments were applied just before flowering: 3 December in Gisborne and 14 December in Marlborough. Two applications were made at each growth stage approximately 2 weeks apart.

Disease Assessment

Pre-labeled bunches were visually monitored throughout the season for the incidence of *botrytis*. Disease assessments were carried out at both sites in late January/early February and again in mid-March, just prior to harvest. On each date the number of *botrytis* infected berries per bunch was recorded. *Botrytis* incidence was low at Marlborough and so bunches were removed from the vine, incubated for 48 h under conditions favourable for *botrytis* development, then assessed. Statistical analysis of results was performed using ANOVA. Before analysis of variance the data were transformed using an angular transformation to stabilise the variance. Analysis of the raw data gave similar conclusions to those of the analysis after transformation, and for simplicity we have presented the raw data.

Results

*Botrytis* Assessment at Gisborne

None of the treatments caused any observable damage to grape tissues at any stage of the season. Frequent rainfall during late January and February in Gisborne facilitated development of *botrytis* in the trial block. At least 70% of bunches had some incidence of *botrytis* at harvest.

*Botrytis* Assessment in Marlborough

In Marlborough conditions remained extremely dry throughout the season and the incidence of *botrytis* was correspondingly low, even when berries were incubated for 48 hours in damp conditions to try and induce *botrytis* using the same technique as reported in Example 5.

Discussion

*U. oudemansii* AGAL No. NM99/06216 was again evaluated for *botrytis* control in grapes (cv. Chardonnay) at vineyards in Gisborne and Marlborough. In Gisborne, conditions were favourable for disease development but the *U. oudemansii* treatment was as effective as the fungicide. These results confirm our earlier findings, as reported in examples 5 and 6. In contrast, conditions in Marlborough were not conducive to *botrytis* infection due to the prolonged drought in this region during the trial. However, some *botrytis* was detected and NM99/06216 reduced disease severity. The level of disease control was again equivalent to that of the fungicide.

These examples illustrate that the biological control agent, *U. oudemansii* AGAL No. NM99/06216 is able to consistently and repeatedly reduce *botrytis* bunch rot in grapes. This was repeated over a range of growing seasons and grape growing regions.

EXAMPLE 8

Efficacy of Other Isolates that Also Belong to the Same *U. oudemansii* Species as AGAL No. NM99/06216

Introduction

Other isolates of *U. oudemansii* have been tested for their ability to control *Botrytis*. The method used for comparing the relative efficacy of these isolates was the same as that described in Example 3.

Methods

Preparation of the leaf disks, spore suspensions, application, timing, and incubation details used for the bioassay were the same as that described in Example 3

Statistical Analysis

Data were subjected to analysis using ANOVA and LSD values were calculated for purposes of mean separation using the GENSTAT statistical package.

Results

Suppression of *Botrytis* spore production with different isolates of *Ulocladium oudemansii* ranged from 82-96% (Table 5).

TABLE 5

The effect of different isolates of *U. oudemansii* on *B. cinerea* development on necrotic kiwifruit leaf tissues in an assay with an interrupted wet period.

| Treatment | % coverage of necrotic leaf tissue by *B. cinerea* conidiophores | |
|---|---|---|
| *B. cinerea* control | 89 | |
| *U. oudemansii* (code HRU G). | 16 | 82[a] |
| *U. oudemansii* (code HRU N) | 4 | 95 |
| *U. oudemansii*) (AGAL No. NM 99/06216] | 3.8 | 96 |
| LSD ($P < 0.05$) | 7.6 | |

[a]Antagonist efficacy, expressed as a percentage reduction of *B. cinerea* conidiophores compared to the *B. cinerea* control treatment.

This example clearly demonstrates that we have tested other isolates of *U. oudemansii* and found that each of them has significantly reduced *Botrytis* development by at least 50%. Two isolates AGAL No. NM99/06216 and *U. oudemansii* (code HRU N) reduced *Botrytis* development by at least 95% in this assay.

REFERENCES

Boff, P. 2000. Epidemiology and biological control of grey mould in annual strawberry crops. PhD thesis. Wageningen University. Wageningen, The Netherlands. 128 pp.

Boyd-Wilson K S H, Perry J H, and Walter M, 1998. Persistance and survival of saprophytic fungi antagonistic to *Botrytis cinerea* on kiwifruit leaves. Proc. 51$^{st}$ New Zealand Plant Protection Conference 51: 96-101.

Butler D, Griffin M J and Fletcher J T, 1979. Leaf spot on cucumber caused by *Ulocladium atrum*. Plant Pathol. 28: 96-97.

Domsch, K. H., Gams, W. and Traute-Heidi Anderson (1980). Ulocladium Preuss 1851 p 825 in Compendium of Soil Fungi Volume 1. Academic Press.

Eden M A, Hill R A and Stewart A, 1996. Biological control of *Botrytis* stem infection of greenhouse tomatoes. Plant Pathology 45: 276-284.

Elad Y, Köhl J, and Fokkema N J, 1994. Control of infection and sporulation of *Botrytis* cinerea in bean and tomato by saprophytic bacteria and fungi. European Journal of Plant Pathology 100:315 336.

Elmer P A G, Walter M, Köhl J, and Boyd-Wilson KSH, 1995. Progress towards biological control of *Botrytis cinerea* in New Zealand kiwifruit orchards. European Journal of Plant Pathology—Abstracts of the XIII International Plant Protection Congress, The Hague, The Netherlands, July 1995, Abstract 1415.

Elmer P A G and Köhl J, 1998. The survival and saprophytic competitive ability of the *Botrytis* spp. antagonist Ulocladium atrum in lily canopies. European Journal of Plant Pathology 104: 435-447.

Gams W, Hoekstra E E and Aptrrot A. 1998. CBS-Course of Mycology, Fourth Edition, Centralbureau voor Schimmelcultures, baarn, 165 pp.

Hill R, Walter M, Elmer P and Kay S, 1998. New methods for controlling *botrytis* in grapes (Abstract). New Zealand Wine Grower Annual Research Supplement 1996/1997 p. 8.

Köhl J, Molhoek W M L, van der Plas C H, and Fokkema N J, 1995a. Effect of *Ulocladium atrum* and other antagonists on sporulation of *Botrytis cinerea* on dead lily leaves exposed to field conditions. Phytopathology 85: 393-401.

Köhl J, Van der Plas CH, Molhoek W M L, and Fokkema N J, 1995b. Effect of interrupted leaf wetness periods on suppression of sporulation of *Botrytis allii* and *B. cinerea* by antagonists on dead onion leaves. European Journal of Plant Pathology 101: 627-637.

Köhl J, Gerlagh M, Haas B H, and Krijger M C, 1998. Biological control of *Botrytis cinerea* in cyclamen with *Ulocladium atrum* and *Gliocladium roseum* under commercial growing conditions. Phytopathology 88: 568-575.

Lennartz B, Schoene P, and Oerke E C, 1998. Biocontrol of *Botrytis cinerea* on grapevine and *Septoria* spp. on wheat. Proceedings 50$^{th}$ International Symposium on Crop Protection Gen 63: 3b 963-970.

Michailides, T and Elmer, P. A. G. 2000. Grey mold of kiwifruit caused by *Botrytis cinerea* in the United States and New Zealand. Plant Disease 84: 208-221

Mimbela-Leyva L, Passam H C, Reilly P J A and Wallbridge A, 1975. Quality Problem of South American Honeydew Melons Imported into Britain. Trop. Sci. 17: 61-74.

Nair, N. G and Allen, R. N. 1993. Infection of grape flowers and berries by *Botrytis cinerea* as a function of time and temperature. Mycological Research 97: 1012-1014

Newhook F J, 1957. The relationship of saprophytic antagonism to control of *Botrytis cinerea* Pers. on tomatoes. New Zealand Journal of Science and Technology A38: 473-481.

Reglinski T, Elmer P, and Hill R, 1998. New methods for suppressing powdery mildew in viticulture (Abstract). New Zealand Wine Grower Annual Research Supplement 1996/1997 p. 7.

Reglinski, T, Elmer P A G, and Hill R A. 1999. *Botrytis* Can we control it ? Proceedings of the 5th Annual Romeo Bragato Conference, Auckland, 26-29 August 1999.

Reglinski T, Elmer P, Wood P, and Hill R, 2000. Integrated use of an elicitor and a fungal antagonist to control *Botrytis* in grapes [Abstract SP42]. Durable Disease Resistance Symposium, Nov. 28-Dec. 1, 2000, Wageningen, The Netherlands.

Schoene P, Lennartz B, Oerke E C, Lyr H (Editor), and Russell P E, 1999. Fungicide sensitivity of fungi used for biocontrol of perthotropic pathogens. pp. 477-482 In: Dehne, H. W. and Sisler, H. D. (Editors) Modern fungicides and antifungal compounds II. 12th International Reinhardsbrunn Symposium. Friedrichroda, Thuringia, Germany 24th-29th May, 1998.

Simmons E G. 1967. Typification of the *Alternaria, Stemphylium* and *Ulocladium*. Mycologia 59: 67-92.

Vanneste, J., Kay, S., Elmer, P. A. G., Reglinski, T and Hill, R. A. 1999. Biological control of economically important diseases in New Zealand. (Poster abstract). International Symposium of Biological Control Agents in Crop and Animal Protection. Swansea, Wales, August 1999

Walter M, Elmer P A G, Boyd-Wilson K S H, Perry J and Köhl J, 1996a. Saprophytic suppression of *Botrytis cinerea* on kiwifruit leaf tissue (Poster abstract). Proc. 49th New Zealand Plant Protection Conference 49: 316.

Walter M, Boyd-Wilson K S H, Elmer P A G, and Köhl J, 1996b. Selection of antagonistic saprophytes for suppression of *Botrytis cinerea* sporulation on kiwifruit tissues (Poster abstract). Proc. 11th International *Botrytis* Symposium 23rd-27th June, 1996, Wageningen, The Netherlands, p. 89.

Wood R K S, 1951. The control of diseases of lettuce by the use of antagonistic organisms. I. The control of *Botrytis cinerea* Pers. Annals Applied Biology 38: 203-216.

Zitter T A and Hsu L W, 1990. A leaf spot of cucumber caused by *Ulocladium cucurbitae* in New York. Plant Disease 74: 824-827.

The invention claimed is:

1. A biological control composition that comprises, in a reproductively viable form and amount, a biologically pure culture of *Ulocladium oudemansii* AGAL No. NM99/06216 effective against a *Botrytis* species and an agriculturally acceptable carrier, diluent or adjuvant.

2. The composition as claimed in claim 1 wherein the strain is present in the form of reproductively viable spores.

3. The composition as claimed in claim 2 wherein the spores are present in a concentration range of from about $1\times10^2$ to $1\times10^7$ spores per ml.

4. The composition as claimed in claim 2 wherein the spores are present in a concentration range of from about $1\times10^3$ to $2\times10^6$ spores per ml.

5. The composition as claimed in claim 4 wherein the spores are present in a concentration range of from about $1\times10^4$ to $2\times10^6$ spores per ml.

6. The composition as claimed in claim 1 which further comprises at least one further strain of *Ulocladium oudemansii* effective against a *Botrytis* species.

7. The composition as claimed in claim 1 wherein the *Botrytis* species is *Botrytis cinerea.*

8. The composition as claimed in claim 1 which further comprises a surfactant.

9. The composition as claimed in claim 8 wherein the surfactant is a polysorbate surfactant.

10. The composition as claimed in claim 8 wherein the surfactant is polyoxyethylenesorbitan monooleate.

11. A biologically pure culture of *Ulocladium oudemansii* AGAL No. NM99/06216.

12. The biological control composition as claimed in claim 1, wherein the composition is in a sprayable, powder or liquid suspension form.

* * * * *